US010668123B2

(12) United States Patent
Deshpande et al.

(10) Patent No.: US 10,668,123 B2
(45) Date of Patent: Jun. 2, 2020

(54) CAPSICUM COMPOSITIONS AND USES THEREOF

(71) Applicant: OmniActive Health Technologies Limited, Mumbai (IN)

(72) Inventors: Jayant Deshpande, Charlottetown (CA); Vijaya Juturu, Morristown, NJ (US); Khadija Ghanam, Charlottetown (CA); Vandita Srivastava, Pune (IN); Jyotish Srivastava, Pune (IN); Sudhakar Akella, Pune (IN)

(73) Assignee: OmniActive Health Technologies Limited, Mumbai (IN)

( * ) Notice: Subject to any disclaimer, the term of this patent is extended or adjusted under 35 U.S.C. 154(b) by 334 days.

(21) Appl. No.: 15/140,054

(22) Filed: Apr. 27, 2016

(65) Prior Publication Data
US 2016/0310555 A1 Oct. 27, 2016

(30) Foreign Application Priority Data
Apr. 27, 2015 (IN) .......................... 1676/MUM/2015

(51) Int. Cl.
| | | |
|---|---|---|
| *A61K 36/81* | (2006.01) | |
| *A61K 31/165* | (2006.01) | |
| *A61K 31/192* | (2006.01) | |
| *A61K 45/06* | (2006.01) | |

(52) U.S. Cl.
CPC ............ *A61K 36/81* (2013.01); *A61K 31/165* (2013.01); *A61K 31/192* (2013.01); *A61K 45/06* (2013.01); *A61K 2236/31* (2013.01); *A61K 2236/33* (2013.01); *A61K 2236/35* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 7,892,582 | B2 | 2/2011 | Verneau |
| 8,663,714 | B2 | 3/2014 | Nielsen et al. |
| 2006/0185034 | A1 | 8/2006 | Todd et al. |
| 2008/0267939 | A1 | 10/2008 | Olalde |
| 2008/0299234 | A1 | 12/2008 | Schrezenmeir |
| 2011/0086829 | A1* | 4/2011 | Zadini .................. A61K 31/575 514/182 |
| 2012/0195988 | A1 | 8/2012 | Rezai-Fard |
| 2012/0219621 | A1 | 8/2012 | Alvarez Favela |
| 2012/0321730 | A1 | 12/2012 | Jacob et al. |

FOREIGN PATENT DOCUMENTS

| | | |
|---|---|---|
| EP | 1902723 | 3/2008 |
| EP | 2329815 | 6/2011 |
| KR | 1020080048426 | 6/2008 |
| KR | 1020130103101 | 9/2013 |
| WO | 2004047717 | 6/2004 |
| WO | 2010128788 | 11/2010 |
| WO | 2015041977 | 3/2015 |

OTHER PUBLICATIONS

Pancal (J. Cardiovasc. Pharmacol. (2011), vol. 57, No. 1, pp. 51-64).*
https://www.nutritionix.com/food/condensed-milk—accessed Jul. 16, 2019.*
Materska et al., "Antioxidant Activity of the Main Phenolic Compounds Isolated from Hot Pepper Fruit (*Capsicum annuum* L.)", Journal of Agricultural and Food Chemistry, vol. 53, 2005, pp. 1750-1756.
Haslam et al., "Obesity", Lancet, vol. 366, 2005, pp. 1197-1209.
Chayasit et al., "Pharmacokinetic and the Effect of Capsaicin in Capsicum frutescens on Decreasing Plasma Glucose Level", J Med Assoc Thai, vol. 92, No. 1, 2009, pp. 108-113.
Tolan et al., "The Effect of Capsaicin on Blood Glucose, Plasma Insulin Levels and Insulin Binding in Dog Models", Phytotherapy Research, vol. 15, 2001, pp. 391-394.
Bloomer et al., "Effect of oral intake of capsaicinoid beadlets on catecholamine secretion and blood makers of lipolysis in healthy adults: a randomized, placebo controlled, double-blind, cross-over study", Lipids in Health and Disease, vol. 3, 2010, 7 pages.
International Search Report and Written Opinion, issued in the corresponding PCT application No. PCT/IB2016/052400, dated Sep. 1, 2016, 8 pages.
Hallmann et al., "Characterization of antioxidant compounds in sweet bell pepper (*Capsicum annuum* L.) under organic and conventional growing systems", Journal of the Science of Food and Agriculture, Sep. 2012, 8 pages (cited in International Search Report).
Chandrasekaran et al., "Review Article: Herbal Approach for Obesity Management", American Journal of Plant Sciences, No. 3, pp. 1003-1014, 2012, available at http://file.scirp.org/pdf/AJPS20120700019_97873259.pdf, (cited in International Search Report).

* cited by examiner

*Primary Examiner* — Susan Hoffman
(74) *Attorney, Agent, or Firm* — Hamre, Schumann, Mueller & Larson, P.C.

(57) ABSTRACT

*Capsicum* compositions are described that include biologically active constituents non-capsaicinoids and capsaicinoids in a specific ratio are useful for the treatment and management of cardiometabolic syndrome and associated risk factors, in a subject in need thereof. The *capsicum* compositions include a *capsicum* extract which is prepared by extracting *capsicum* pods by using suitable polar and non-polar solvents. *Capsicum* compositions include non-capsaicinoid components like saponins and polyphenols such as flavonoids, which along with capsaicinoids effectively reduce risk factors of cardiometabolic syndrome and also reduce oxidative stress on vital body organs by reducing inflammatory and/or oxidative markers. The *capsicum* compositions inhibit pancreatic lipase enzyme and enhance lipolysis, when administered in an effective amount to a subject in need thereof. *Capsicum* compositions as described herein are prepared by human intervention and are safe for consumption.

6 Claims, 5 Drawing Sheets

CAPSICUM COMPOSITIONS AND USES THEREOF

FIELD

*Capsicum* compositions comprising non-capsaicinoids and capsaicinoids in a ratio of at or about 1:0.1 to at or about 1:10 are described herein for the treatment and management of cardiometabolic syndrome and associated risk factors from which a subject may be suffering and may be in need of a treatment. The compositions are comprised of *capsicum* extract, including compounds such as capsaicinoids and non-capsaicinoids in a specific ratio. Non-capsaicinoids comprised in the composition include saponins and/or polyphenols, such as flavonoids. Processes for preparation of *capsicum* compositions are described herein that use food grade polar and non-polar solvents. More particularly, *capsicum* compositions herein comprise biologically active constituents including saponins and/or polyphenols, and including capsaicinoids, which are useful for prevention and treatment of cardiometabolic syndrome such as hyperlipidemia, hypertension, hyperglycemia and other cardiovascular disorders. *Capsicum* compositions described herein improve cardiometabolic syndrome and manage associated risk factors such as body weight, body fat, lipid profile, blood glucose levels and the like, when administered to a subject in need thereof, in an effective amount. The composition also improves cardiovascular endothelial function by reducing oxidative stress and inflammatory markers. *Capsicum* compositions described herein can reduce cardiometabolic stress in a subject, in need thereof, by inhibiting pancreatic lipase enzyme and enhancing lipolysis. The composition is safe for consumption and can be employed for management of cardiometabolic syndrome, when administered in an effective amount.

BACKGROUND

The recognition of metabolic syndrome as a major and prevalent cause of coronary heart disease has helped to understand a key concept based on pathophysiology, such as insulin resistance, and to connect it with other related risk factors that can be diagnosed by primary care physicians. The importance of insulin resistance as a core metabolic abnormality is associated with a constellation of cardiovascular and diabetogenic risk factors/markers, and is also recognized and linked to abdominal obesity. In patients likely to have excess abdominal fat, attention has been paid to five parameters (waist circumference, triglycerides, high density lipoprotein (HDL)-cholesterol, fasting glycemia, blood pressure) in order to identify individuals with metabolic syndrome, more specifically cardiometabolic syndrome. In many cases measurement of waist circumference over body mass index (BMI) is recommended when estimating the amount of abdominal fat. This recommendation to measure waist circumference or waist to hip ratio was a giant conceptual leap forward in clinical practice, as it recognized abdominal obesity as a prevalent form of the cardiometabolic syndrome for example in affluent, sedentary populations.

Cardiometabolic syndrome (CMS) is thus a clustering of interrelated risk factors that promote the development of atherosclerotic vascular disease and type 2 diabetes mellitus, as a result of imbalance between energy intake and utilization. Individuals with cardiometabolic syndrome are at high risk of developing heart failure and glucose intolerance, thus affecting vital organs such as the eye, liver, kidney and nervous system. The prevalence of obesity is increasing at an alarming rate in developed and developing countries (Haslam and James, 2005). Obesity makes it more difficult for cells to respond to insulin. If the body cannot make enough insulin to override the resistance, the blood sugar level increases and diabetes can result.

The sedentary nature of work, anxiety, and/or stress, and also coupled with increased intake of high fat and high carbohydrate seems to have an impact on the development of cardiometabolic disorder. Free radical generation and oxidative stress is the main cause of developing associated risk factors of cardiometabolic syndrome. Hence natural antioxidant supplementations and exercise can be potential therapeutic measures to protect vital body organs from dreadful effects of oxidative stress and anxiety and to combat cardiometabolic syndrome.

In recent years certain chemical constituents found in natural products have attracted the interest of researchers because they show promise of being powerful antioxidants that can protect the human body from free radicals, the formation of which is associated with the normal natural metabolism of aerobic cells (Matereska 2005). The antiradical activity of compounds such as flavonoids and phenolics is principally based on the redox properties of their hydroxy groups and the structural relationships between different parts of their chemical structure. Such compounds cannot be produced by the human body and thus must be taken in mainly through the daily diet. Many such compounds having antioxidant properties are found in pepper fruits (*Capsicum annuum* L.) which are vegetables used as foods and as spices. Peppers are a good source of vitamins C and E as well as provitamin A. Many references deal with evaluation of *capsicum* compositions in health applications.

European patent application EP2329815A1 relates to a *Capsicum annuum* paprika plant extract composition comprising zeaxanthin, wherein zeaxanthin is the predominant carotenoid, and wherein the *Capsicum annuum* paprika plant is obtained by classical plant breeding methods. The *Capsicum annuum* paprika plant extract composition is used for ingestion for the treatment or the prevention of human or animal diseases including cancer-related diseases, inflammatory disorders and nervous system diseases.

Another EP patent application EP1902723A1 relates to pungent principles such as *capsicum*, garlic and/or *sabal*, as such or in the form of extracts or essential oils which are used as an antidiabetic, lipase inhibitor and as an anorectic.

U.S. patent application publication US20120219621 describes a composition comprising: a) menthol or a peppermint essential oil comprising menthol, in association with one or more components having a thermogenetic activity, selected from: b1) capsaicin or a capsacinoid derived from *Capsicum* genus or a *Capsicum* extract containing capsaicin and/or capsacinoids; b2) a sulphur containing active principle derived from the *Allium* genus or an *Allium* extract containing it; b3) a catechin active principle derived from the genus *Camellia*, or a *Camellia* extract containing it, for use in the treatment and prevention of obesity, overweight, metabolic syndrome, hypercholesterolemia, hypertriglyceridemia, diabetes or hypertension. This application deals with synergistic effects of menthol or essential oil in association with either *capsicum* extract or sulphur or catechin for said health benefits.

Korean application KR1020130103101 describes a composition for body fat lipolysis using alginate double-layer nanoemulsions containing *oleoresin capsicum* to resolve problems such as overweight and obesity. A method for manufacturing the alginate double-layer nanoemulsion composition comprises the steps of: mixing *oleoresin capsicum* and Tween 80 in a ratio of 1:3 to prepare a mixture solution; and mixing the mixture solution and an alginic acid solution to prepare double-layer nanoemulsions.

U.S. Pat. No. 7,892,582 describes a composition for oral administration containing capsaicinoids associated with a formulation base acceptable for oral administration, the formulation base comprising an oil and an additive solid or pasty at room temperature. Further it discloses a method for stimulating thermogenesis, treating obesity, digestive problems, or for reducing the appearance of cellulite comprising administering the said composition.

Korean patent application KR1020080048426 describes an anti-obesity composition containing fresh red pepper (*Capsicum annuum* L.) extract as an active ingredient. The composition contains 20 to 100% by weight of fresh red pepper extract, 20 to 80% by weight of a corn silk extract, 0.5 to 10% by weight of *Pueraria* root extract and 0.5 to 10% by weight of garlic extract.

PCT patent application WO2015041977 describes a composition comprising at least two compounds capable of enhancing thermogenesis or identified as capable of enhancing thermogenesis, wherein the composition comprises one non-stimulant and at least one stimulant. The non-stimulant thermogenic agent is an agent selected from the group consisting of: a) fucoxanthin; b) branched-chain amino acid; c) decaffeinated tea, decaffeinated tea extract, or isolated component or components from decaffeinated tea; and d) capsaicin extract or isolated component or components from capsaicin extracts.

PCT application WO2010128788 relates to anti-obesity external dermal agent compositions containing capsaicin or capsaicin-like compounds as active ingredients. The anti-obesity external dermal agent compositions containing capsaicin or capsaicin-like compounds stimulate the metabolism of the body to decompose the fat cells of subcutaneous fat, and inhibit body fat accumulation to reduce hypertrophy of fatty tissues, thus eventually reducing weight and efficiently preventing and improving obesity.

U.S. patent application publication US20120321730 provides an industrial process for isolation and purification of capsanthin rich carotenoid mixture from paprika *oleoresin* extracted from *Capsicum annuum*. Further it discloses a method of using *Capsicum annuum* extract for a cosmetic application, as a nutraceutical, as an antioxidant, or as a health supplement, where the method comprises contacting the extract or the composition with a subject in need thereof.

U.S. Pat. No. 8,663,714 relates to a dietary supplement for treating obesity in a human in need thereof consisting essentially of therapeutically effective amounts of alginate, *Capsicum frutescens* extract, *Mentha piperita* extract and glucomacropeptide. Extracts of chili (*Capsicum* species) and mint (*Mentha* species) can be encapsulated into beads of alginate gel.

PCT application WO2004047717 relates to a topical application of Curcumin (from *Curcuma longa*, Turmeric) alone or in combination with Capsaicin (*Capsicum oleoresin*) for treating peripheral neuropathies, including diabetic neuropathy associated with chronic type I or Type II diabetes mellitus.

Chaiyasit et al (J Med Assoc Thai. 2009 January; 92 (1):108-13) relates to the effect of *capsicum* on plasma glucose level and to correlate its action with the pharmacokinetic properties of capsaicin in *capsicum*. The results showed that plasma glucose levels in volunteers who received *capsicum* were significantly lower than those in the placebo group.

Tolan et al (Phytother Res. 2001 August; 15 (5):391-4) describes the effect of capsaicin from *Capsicum frutescens* on blood glucose, plasma insulin levels and insulin binding in dog models. This study was designed to identify any hypoglycaemic principle(s) and to determine the mechanism of action. It was observed that capsaicin is responsible for the hypoglycaemic episodes seen in the dogs and that it also causes an increase in insulin secretion which leads to a reduction of insulin binding on the insulin receptors.

Bloomer et al (Lipids Health Dis. 2010 Jul. 15; 9:72) describes effect of oral intake of capsaicinoid beadlets on catecholamine secretion and blood markers of lipolysis in healthy adults. Blood epinephrine (EPI), norepinephrine (NE), free fatty acids (FFA) and glycerol concentrations were compared in response to a capsaicinoid supplement or placebo in healthy adults before and after acute exercise. Ingestion of low dose (2 mg) *Capsicum* composition was associated with an increase in blood FFA and glycerol at selected times post ingestion, as compared to placebo. However, the composition had no differing effect on EPI or NE compared to placebo.

SUMMARY

Even though the references above discuss the effect of *capsicum* in thermogenesis, body fat reduction, and neuropathy as well as for reducing body weight, there is no discussion on the chemical constituents of a *capsicum* composition which exert these and other related biological activities. Even though there are some descriptions on commonly found chemical constituents such as capsaicinoids in literature and their possible effect in weight management, there are no reports to date which focus on characterization of *capsicum* extracts for identification of a specific combination of capsaicinoids and non-capsaicinoid constituents, such as flavonoids and saponins, and in a specific ratio, which exhibit beneficial biological effects in the body systems, such as the cardiovascular system.

Applicant has carried out rigorous experimentation and optimization for preparation and characterization of *capsicum* extract compositions, as described herein. The extract compositions herein were characterized for identification of chemical constituents by employing sophisticated analytical techniques. *Capsicum* extract compositions herein are further evaluated for exploring effect in preventing and treating cardiometabolic syndrome by effectively reducing multiple risk factors and co-relating the chemical constituents identified to this biological activity, which is not reported anywhere in to date.

*Capsicum* compositions herein are comprised of a *capsicum* extract, including biologically active chemical constituents, such as non-capsaicinoids and capsaicinoids in a specific ratio, where the non-capsaicinoids are further comprised of saponins and/or polyphenols such as flavonoids.

In an embodiment, a *capsicum* composition herein is characterized by different analytical methods to identify capsaicinoids, polyphenols and saponins. Major capsaicinoids such as capsaicin and dihydrocapsaicin and other capsaicinoids, such as nor dihydrocapsaicin, N-vanillyldecanamide, dihydrocapsaicin, homocapsaicin are identified and quantified along with non-capsaicinoid compounds. Non-capsaicinoid compounds such as polyphenols and saponins are identified from the *capsicum* compositions herein. Polyphenols may be comprised of flavonoids and cinnamic acid derivatives in the composition described herein. Capsaicinoids such as capsaicin and dihydrocapsaicin are called major capsaicinoids, which are present in a range of at or about 25 to at or about 35% w/w in the composition. Other capsaicinoids are present in amount of at or about 0.5 to at or about 1.5% w/w, in the composition. The compositions as described herein also contain total polyphenols comprising flavonoids and cinnamic acid derivatives, in the range of at or about 10 to at or about 20% w/w. The compositions herein are also analyzed for saponin content and found to be in the range of at or about 0.1 to at or about 5% w/w. *Capsicum* compositions herein are safe for human consumption and are comprised of biologically active chemical constituents including non-capsaicinoids and capsaicinoids in the ratio of at or about 1:0.1 to at or about 1:10, where such a specific ratio manages cardiometabolic syndrome when administered to a subject in an effective amount.

*Capsicum* compositions described herein when administered in an effective amount to a subject in need thereof, helps to improve cardiometabolic syndrome and manages associated risk factors such as body weight, body fats, lipid profile, blood glucose and the like. The compositions herein also improve cardiovascular endothelial function by reducing oxidative stress and inflammatory markers. *Capsicum* compositions described herein can reduce cardiometabolic stress in a subject, in need thereof, by inhibiting pancreatic lipase enzyme and enhancing lipolysis. The compositions herein are prepared by human intervention using food grade solvents, it is safe for human consumption, and can be employed for management of cardiometabolic syndrome, when administered in effective amounts.

In an embodiment, a *capsicum* compositions is provided having a specific ratio of saponins and/or polyphenols to capsaicinoids, which when administered in an effective amount to a subject in need thereof, are useful for management of cardiometabolic syndrome and associated risk factors.

In an embodiment, a *capsicum* composition herein comprises *capsicum* extract, including capsaicinoids and non-capsaicinoids. The capsaicinoids are selected from the group of, but not limited, capsaicin, dihydrocapsaicin, nordihydrocapsaicin, homocapsaicin, dihydrohomocapsaicin, 6'',7''-dihydro-5',5'''-dicapsaicin, 5,5'-dicapsaicin, decaylvanillamide, and combinations thereof. The non-capsaicinoid compounds are saponins and polyphenols such as flavonoids, which are biologically active compounds, identified for their effect in management of cardiometabolic syndrome, when administered in an effective amount.

In an embodiment, a *capsicum* extract for the *capsicum* composition is prepared from various varieties of paprika selected from the group of, but not limited to, varieties such as for example Teja and Namdhari. More particularly, the composition herein may be comprised of the *capsicum* extract obtained from varieties of *Capsicum annum* such as Teja and Namdhari.

In an embodiment, an industrially viable process is provided for preparation of a *capsicum* composition by employing non-polar, semi-polar, polar solvents or combinations thereof in suitable ratios. In an embodiment, a *capsicum* composition is prepared using a combination of polar and non-polar solvents in a suitable ratio for an extraction cycle, followed by purification of the extract by using polar solvent(s) to obtain the extract. The composition including the extract is safe for human consumption and is comprised of biologically active chemical constituents including capsaicinoids and non-capsaicinoids, which are useful for management of cardiometabolic syndrome in subjects, when administered in effective amounts.

In an embodiment, a *capsicum* composition is comprised of chemical constituents, which are characterized by various analytical methods.

In an embodiment, a *capsicum* composition which is prepared by using *capsicum* extract, either alone or in combination with other nutrients such as capsanthin, capsanthin-ester, betacryptoxanthin, betacarotene, capsorubin, zeaxanthin, antheraxanthin, and/or at least one more pharmaceutically or nutraceutically acceptable excipients, and formulating it into a suitable delivery form for oral or non-oral route of administration.

In an embodiment, methods for use of the *capsicum* compositions herein are provided that comprise administering to a subject in need thereof an effective amount of biologically active constituents including capsaicinoids and non-capsaicinoids, and evaluating its effects on management of cardiometabolic syndrome and the associated risk factors.

In an embodiment, methods for use of the *capsicum* compositions herein are provided that comprise administering to a subject in need thereof an effective amount of biologically active constituents in managing, treating or improving conditions, including one or more of hypertension, hyperlipidemia, hyperglycemia, insulin resistance, obesity, waist to hip ratio, and the like, associated with cardiometabolic syndrome.

DETAILED DESCRIPTION

Figure 1:
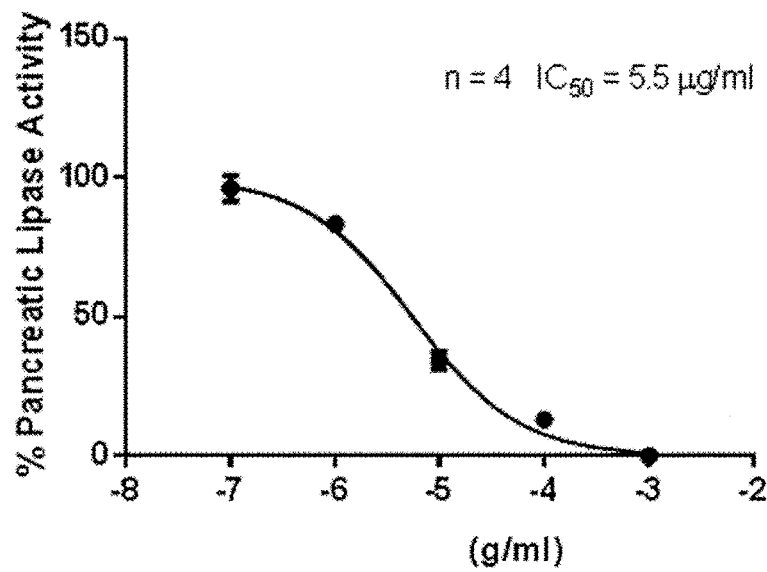
FIG. 1 shows a graph of the effect of *capsicum* composition on pancreatic lipase enzyme.

Compositions, methods of their preparation, and methods of their use herein are directed to *capsicum* compositions comprising specific biologically active chemical constituents, which are effective in treating and/or managing cardiometabolic syndrome and their associated risk factor(s). The compositions are comprised of capsaicinoids and non capsaicinoids. Further capsaicinoids are one or more selected from the group of compounds, but are not limited to, capsaicin, dihydrocapsaicin, nordihydrocapsaicin, homocapsaicin, dihydrohomocapsaicin, 6'',7''-dihydro-5',5'''-dicapsaicin, 5,5'-dicapsaicin, and N-vanillyldecanamide. Non-capsaicinoid compounds include polyphenols and/or saponins, where the capsaicinoids and non-capsaicinoids are present in a specific ratio. Polyphenols present in *capsicum* composition herein may be in the form of flavonoids and cinnamic acid derivatives. The compositions described herein are comprised of biologically active chemical constituents which are useful for managing cardiometabolic syndrome and associated risk conditions such as body weight, lipid profile, insulin resistance and blood glucose and the like, when administered in an effective amount to a subject in need thereof. The compositions herein exhibit reduction in oxidative stress and inflammatory markers, enhance lipolysis, and inhibit pancreatic lipase when administered to a subject in an effective amount.

*Capsicum* compositions herein are obtained by human intervention, using conventional industrial equipments and are safe for human administration and thus are useful for nutraceutical purposes. In an embodiment, the solvents employed, which can include for example but not limited to hexane and acetone, obtain the specific *capsicum* extract having non-capsaicinoids and capsaicinoids in a specific ratio range, which may be used in a *capsicum* composition.

Cardiometabolic syndrome, also known as syndrome X, increases the risk of developing cardiovascular disease, particularly atherosclerosis, heart failure, dyslipidemia, diabetes, and associated risk factors, which may be caused mainly due to imbalance of calorie intake and energy utilization. One of the most important causes for this is dietary habits.

The terminology 'subject' is commonly used herein to refer to an individual or mammal under test, being treated with compositions herein. The terminology "subject in need thereof" can include specific individuals or mammals, which may be or are habituated to a diet rich in high fat and refined carbohydrates, thus lacking in fibers. Such subjects are at high risk of developing and/or may be suffering from cardiometabolic syndrome, because of developing abdominal obesity. These subjects also exhibit disturbed body parameters related to blood glucose, body fat, lipid profile, increased body weight, and may be prone to cardiovascular diseases.

The terminology "capsaicinoids" as used herein refers to the chemical compounds identified in *capsicum* extract prepared for example from paprika variety, which belong to classes selected from, but not limited to, capsaicinoids, dicapsaicinoids, capsaicin, nor dihydrocapsaicin, N-vanillyldecanamide, dihydrocapsaicin, homocapsaicin their derivatives, salts, and the like.

The term "non-capsaicinoids" as used herein refers to the chemical compounds identified from *capsicum* extract, which belong to classes other than capsaicinoids and these compounds can be saponins, polyphenols such as cinnamic acid derivatives and flavonoids, and the like, which in combination with capsaicinoids exert biological activity and are effective in treatment and management of cardiometabolic syndrome, when administered in an effective amount to a subject in need of treatment thereof.

Abdominal obesity can drive the progression of multiple risk factors directly, through the secretion of excess free fatty acids and inflammatory adipokines, and decreased secretion of adiponectin. For example, excess abdominal obesity is accompanied by elevated levels of C-reactive protein (CRP) and free fatty acids (FFAs), as well as decreased levels of adiponectin. Elevated CRP is an indicator of inflammation. Abdominal obesity may be associated with the inflammation cascade, with adipose tissue expressing a number of inflammatory cytokines. Inflammation is now believed to play a role in the development of atherosclerosis and type 2 diabetes. Elevated levels of CRP are considered to be predictive of cardiovascular disease and insulin resistance.

Low-grade chronic inflammation is characterized by a two- to threefold increase in the systemic concentrations of cytokines such as tumor necrosis factor alpha (TNF-α), interleukin 6 (IL-6), and/or CRP. TNF's primary role is to regulate the immune cells and induce inflammation. TNFα-induced reductions in insulin sensitivity in adipocytes are partly responsible for the increased free fatty acid production and hypertriglyceridaemia characteristic of abdominal obesity. Leptin responds specifically to adipose-derived inflammatory cytokines. Hyperglycemia induces IL-6 production from endothelial cells and macrophages. Meals high in saturated fat, as well as meals high in calories have been associated with increases in inflammatory markers.

In an embodiment, *capsicum* compositions and methods of use thereof, when administered to a subject in need thereof, in an effective amount, are able to treat and/or manage risk factors associated with cardiometabolic syndrome.

In an embodiment, a *capsicum* composition is comprised of a *capsicum* extract prepared for example from various varieties of paprika, which is further comprised of chemical constituents including non-capsaicinoids in combination with capsaicinoids in a ratio of at or about 1:0.1 to at or about 1:10. Thus, *capsicum* compositions herein are comprised of *capsicum* extract rich in biologically active constituents such as capsaicinoids and non-capsaicinoids including for example, saponins and/or flavonoids, which the extract is formulated into a suitable dosage form and/or delivery system, by combining with one or more other nutrients and/or with one or more other pharmaceutically or nutraceutically acceptable excipients.

According to an embodiment, *capsicum* compositions are comprised of a *capsicum* extract herein and one or more nutraceutically acceptable excipient such as but not limited to diluents, carrier, binder, stabilizer, solubilizer, coating, glidant, lubricant and the like or combinations thereof. It may further comprise one or more nutrients such as but not limited to carotenoids, omega-3-fatty acids, vitamins, minerals.

According to an embodiment, *capsicum* compositions are also comprised of a *capsicum* extract herein and one or more nutrients, formulated along with at least one more pharmaceutically or nutraceutically acceptable excipient selected from the group of, but not limited to diluent, antioxidant, binder, film former, carrier, buffer, vehicle, stabilizer, surfactant, glidant, filler and the like or combinations thereof.

According to an embodiment, a *capsicum* extract is prepared from different varieties of raw paprika such as but not limited to Teja and/or Namdhari by employing organic and/or inorganic solvents selected from the group of, but not limited to polar, semi-polar and non-polar solvents or combinations thereof.

As per an embodiment, a *capsicum* extract is prepared by extracting deseeded and pulverized raw paprika with a combination of polar and non-polar solvents. Polar solvents used in the process may be selected from the group of, but not limited to, alcohol, water, acetone, ethyl acetate, acetonitrile, dimethylformamide, tetrahydrofuran and the like, either alone or in combinations thereof.

As per an embodiment, a *capsicum* extract is prepared by extracting paprika using a non-polar solvent selected from the group of, but not limited to, pentane, hexane, cyclohexane, diethyl ether, and the like, either alone or in combinations thereof.

In an embodiment, a *capsicum* extract is prepared by employing a combination of polar and non-polar solvent in a ratio of at or about 1:0.5 to at or about 1:10 by weight.

In an embodiment, the ratio of raw material, e.g. paprika, to solvent employed is at or about 1:0.5 to at or about 1:20 by weight in each extraction cycle. In an embodiment, a sufficient number of extractions are carried out followed by percolation.

As per an embodiment, a *capsicum* composition comprises an extract prepared by extracting raw material, e.g. paprika, employing a combination of polar and non-polar solvents, such as for example but not limited to acetone and hexane, in a suitable ratio, in each extraction cycle and an extracted mass from the extractions are combined, distilled and concentrated. Crude extract thus obtained is washed with polar solvents, such as for example but not limited to alcohol and water to obtain purified *capsicum* extract, which can be either used alone or in the form of a dosage form, prepared by using at least one excipient and carrier, for convenient administration to the subject in need thereof.

According to an embodiment, *capsicum* extract is characterized by one or more analytical techniques such as but not limited to TLC (thin layer chromatography), MS (Mass spectroscopy), gravimetric analysis, UV spectrophotometry, and other suitable techniques for identification of capsaicinoids and non-capsaicinoid compounds in a resulting extract or composition including the resulting extract.

According to an embodiment, *capsicum* compositions herein comprise an extract that can be formulated as a pharmaceutical or nutraceutical delivery systems, in the form of a dietary supplement, a dosage form, or in suitable vehicle, convenient for administration. The compositions herein can be administered in the form of powders, granules, sachets, beadlets, tablets, capsules, caplets, suspensions, emulsions, solutions, energy bar, beverages, functional foods and the like.

*Capsicum* compositions herein may be administered by oral route or other suitable routes other than oral, in combination for example with an antioxidant or one or more other nutrients, using a suitable vehicle for administration.

As per an embodiment, the compositions described herein are comprised of biologically active chemical constituents, which can help to improve risk factors associated with cardiometabolic syndrome, such as body weight, lipid profile, body glucose, and/or insulin resistance, when administered to a subject in need thereof and in an effective amount.

As per an embodiment, the methods described herein are directed to identifying a subject in need thereof, for treatment, prevention or improvement of a condition or risk factor associated with cardiometabolic syndrome, and administering to the subject a *capsicum* composition, comprising biologically active constituents, in an effective amount.

In an embodiment, a *capsicum* composition is characterized by different analytical method(s) to identify capsaicinoids and non-capsaicinoids, e.g. polyphenols and saponins, present. Major capsaicinoids such as capsaicin and dihydrocapsaicin and other capsaicinoids such as nor dihydrocapsaicin, N-vanillyldecanamide, dihydrocapsaicin, homocapsaicin are identified and quantified along with non-capsaicinoid compounds. Non-capsaicinoid compounds such as polyphenols and saponins are identified from the *capsicum* composition. Polyphenols may be comprised of flavonoids and cinnamic acid derivatives in the composition described herein. Capsaicinoids such as capsaicin and dihydrocapsaicin are called as major capsaicinoids which are present in range of at or about 25 to at or about 35% w/w in the composition. Other capsaicinoids are present in amount of at or about 0.5 to at or about 1.5% w/w, in the compositions. The compositions as described herein also contain total polyphenols comprising flavonoids and cinnamic acid derivatives, in the range of at or about 10 to at or about 20% w/w. The compositions are also analyzed for saponin content and found to be in the range of at or about 0.1 to at or about 5% w/w. Thus *capsicum* compositions are comprised of non-capsaicinoids and capsaicinoids in the ratio of at or about 1:0.1 to at or about 1:10, where such compositions with this specific ratio range of biologically active chemical constituents are useful for treatment and/or management of cardiometabolic syndrome.

According to an embodiment, *capsicum* compositions are comprised of at or about 0.01% to at or about 75% bioactive compounds by weight in the *capsicum* extract.

According to an embodiment, *capsicum* compositions comprising capsaicinoids and non-capsaicinoid compounds are administered in an effective amount, such as, but not limited to, at or about 0.5 mg to at or about 10 mg/kg body weight to a subject in need thereof.

According to an embodiment, *capsicum* compositions comprising at or about 0.01 to at or about 75% biologically active compounds by weight of the *capsicum* extract, are administered to a subject in need of treatment of cardiometabolic syndrome, in the form of a dietary supplement either alone or optionally in combination with one or more other ingredients selected from the group of, but not limited to lipid lowering, blood sugar lowering, and/or blood pressure lowering ingredients, and the like or combinations thereof.

As per an embodiment, *capsicum* compositions and methods herein can treat hyperlipidemia, in a subject in need thereof, when administered in an effective amount, by lowering total cholesterol, low density lipoproteins and/or triglycerides.

According to an embodiment, compositions and methods herein are directed to reducing free fatty acid levels, and/or visceral fat, along with body weight, when administered in an effective amount to a subjects in need thereof.

According to an embodiment, *capsicum* compositions described herein are also effective in inhibiting fat absorption by inhibition of pancreatic lipase and enhancement of lipolysis and thermogenesis, when administered in an effective amount, to a subject in need thereof.

According to an embodiment, *capsicum* compositions described herein are effective to improve post-prandial hypoglycemia and insulin sensitivity in a subject in need thereof by the reduction in body glucose levels and/or the reduction in insulin resistance and are effective to protect vital body organs, when administered in an effective amount.

According to an embodiment, *capsicum* compositions and methods herein are also used to treat and/or evaluate their effect on expression of inflammatory markers and/or oxidative stress markers, when administered to a subject in need thereof. The compositions are also evaluated in cell line studies for checking effect on enzymes or cardiometabolic markers. The evaluation is also carried out in human volunteers for their effect on various enzymes and effect on body fats, blood pressure, waist to hip ratio, appetite and other cardiometabolic risk factors that affect management of cardiometabolic syndrome.

For evaluation purposes, the *capsicum* compositions herein may be administered in the form of semi-solid concentrates, being suspended in a suitable oil vehicle, or as a formulation such as beadlets or capsules. The formulation may be also referred to as "Capsimax" or "CAPs" hereinbelow to denote the *capsicum* compositions, which includes the *capsicum* extract.

In an embodiment, compositions and methods herein are directed to evaluating the effect(s) of a *capsicum* composition on the improvement of cardiometabolic health by administering to a subject in need thereof, an effective amount of a composition comprising *capsicum* alone or in combination with other nutrients.

In an embodiment, *capsicum* compositions herein and methods of use thereof are directed to the improvement of cardiometabolic health by management of a healthy lipid profile, reduction in body fat, visceral fat, and free fatty acid levels in the body.

In an embodiment, *capsicum* compositions herein and methods of use thereof are directed to administering the composition in an effective amount, to a subject in need thereof, for the treatment and/or management of cardiometabolic syndrome, to improve lipid profile, to reduce body weight, and/or to reduce oxidative stress markers in the vital body organs.

In an embodiment, *capsicum* compositions and methods of use thereof are directed to reducing risk factors associated with cardiometabolic syndrome, such as for example obesity, hyperglycemia, hypertension, and/or hyperlipidemia, and the like.

In an embodiment, compositions herein include a *capsicum* extract administered either alone or in the form of a composition with one or more other nutrients and/or food grade excipients. Other nutrients in *capsicum* compositions can include but are not limited to capsanthin, capsanthin-ester, betacryptoxanthin, betacarotene, capsorubin, zeaxanthin, antheraxanthin. Compositions herein include an extract comprising biologically active constituents including capsaicinoids and non-capsaicinoids.

The compositions herein may be administered as a daily dose for a period of about 7 days to about 12 months. In an embodiment, administration of the composition is with meal(s).

*Capsicum* compositions, as described herein are safe for human consumption and are prepared using food grade solvents. The *capsicum* compositions herein are comprised of biologically active chemical constituents including non-capsaicinoids and capsaicinoids in a ratio of at or about 1:0.1 to at or about 1:10, and are useful for management of cardiovascular syndrome and associated risk factors, when administered in an effective amount to a subject in need thereof. The compositions herein are analyzed for identification of chemical constituents, and also evaluated for biological activity through in-vitro and in-vivo evaluations.

While the compositions and methods herein have been described in terms of specific illustrative embodiments, any modifications and equivalents that would be apparent to those skilled in the art are intended to be included within the scope of the compositions and methods herein. The details of the compositions and methods herein, its objects, and advantages are explained hereunder in greater detail in relation to non-limiting exemplary illustrations.

EXAMPLES

Example 1: Preparation of *Capsicum* Composition

*Capsicum* composition is prepared by extracting dried pods of *capsicum* annum with a combination of acetone and hexane in a ratio of 1:0.5 to 1:10 by weight and subjected to filtration. The ratio of raw material to solvent employed is about 1:0.5 to 1:20 by weight in each extraction cycle. Sufficient numbers of extractions are carried out at suitable process conditions followed by percolation. Extracted mass from all such extractions are combined, distilled and concentrated. Crude extract thus obtained is washed with suitable polar solvents to get purified *capsicum* composition. This method was used for preparation of all three batches CC1 to CC3 as shown in Table No. 1. The dose amounts referred to in the tests hereinbelow are to the amount of the *capsicum* extract, which has a specific ratio of non-capsaicinoids to capsaicinoids. The *capsicum* extract is obtained in the form of a semi-solid concentrate, which is evaluated in the following Examples. It will be appreciated that the *capsicum* extract may be further formulated into other forms, such as but not limited to beadlets, powders, oil suspensions. Reference to capsimax and CAP in the descriptions and drawings herein are to the *capsicum* extract obtained in the form of a semi-solid concentrate.

Example 2 a: Determination of *Capsicum* Composition for Capsaicinoids

*Capsicum* composition is analyzed by a high performance liquid chromatography (HPLC) method using Thermo C18 column at 281 nm detector wavelength. Methanol was used as a diluent and a mobile phase was prepared using 0.1% Ortho Phosphoric Acid in Water and acetonitrile in a ratio of 600:400. Capsaicin solution was used as a standard, which was prepared by dissolving reference standard in methanol. About 25 mg of *capsicum* composition was accurately weighed and diluted with methanol to obtain a test solution.

Equal volumes of standard Capsaicin solution, standard dihydrocapsaicin solution, and test solution were separately injected into the chromatograph and the area of the responses for all of the peaks was measured to calculate the percentage of capsaicin, dihydrocapsaicin, and other capsaicinoids.

Example 2 b: Determination of *Capsicum* Composition for Non-Capsaicinoids (Polyphenols)

Polyphenol content was determined as total polyphenol content (as Gallic acid equivalent) by UV spectrophotometry technique by Folin-Ciocalteau's phenol reagent method. *Capsicum* composition is dispersed in methanol in desired concentration and 1.0 ml of each sample is taken into test tube and mixed with 5 ml of a 10 fold dilute Folin-Ciocalteu reagent and 4 ml of 7.5% sodium carbonate. The tubes are covered with parafilm and allowed to stand for 50 minutes at room temperature. Then the absorbance was read at 765 nm spectrometrically against Gallic acid as a standard.

Flavonoids were identified by a liquid chromatography-mass spectroscopy (LC-MS) method from batch CC3 and the compound was identified as Apigenin 6-C-β-D-glucopyranoside-8-C-α-L-arabinopyranoside.

Example 2 b: Determination of *Capsicum* Composition for Non-Capsaicinoids (Saponins)

Saponins were quantified using a gravimetric method. *Capsicum* composition was extracted with methanol by refluxing for an hour and the resulting residue was extracted two more times by using methanol. Methanolic extract was combined and precipitated with acetone. The precipitate was filtered and weighed.

TABLE NO. 1

Chemical composition (% w/w) of capsicum composition

| Composition | Capsaicin | Nor dihydro-capsaicin | N-vanillyl decanamide | Dihydro-capsaicin | Homo-capsaicin | Total capsaicinoids as capsaicin | Total Polyphenol (As Gallic acid) | Total Saponins |
|---|---|---|---|---|---|---|---|---|
| CC1 | 20.65 | 0.83 | 0.0004 | 10.98 | 0.0002 | 32.46 | 13.36 | 1.09 |
| CC2 | 19.09 | 1.62 | 0.0099 | 13.61 | 0.0000 | 34.33 | 15.96 | 0.89 |
| CC3 | 21.00 | 1.00 | 0.0042 | 10.95 | 0.0004 | 32.95 | 13.90 | 0.95 |

(cc-capsaicin composition)

The *Capsicum* composition is comprised of:
1) Major Capsaicinoids (e.g. Capsaicin and/or Dihydrocapsaicin)=between 25-35% w/w.
2. Other Capsaicinoids (Nor dihydrocapsaicin and/or N vanillyldecanamide and/or+Homocapsaicin)=between 0.5-1.5% w/w.
3. Total Polyphenols (As gallic acids)=between 10 to 20% w/w.
4. Total saponins=between 0.1 to 5%
Ratio of non-capsaicinoids: capsaicinoids=1:01 to 1:10

Example 3: Evaluation of *Capsicum* Composition for Activity on Pancreatic Lipase Enzyme Study Using Fluorescence Assay:

Pancreatic lipase activity was measured using 4-methylumbelliferyl oleate (MU Oleate) as a substrate via a fluorescence kinetic assay. 3T3L1 cells were treated with *capsicum* composition (100 µg/1111) at different time points such as 1 hour (h), 2 h, 4 h and 24 h. Orlistat was used as the positive control. Lipolysis was assessed using glycerol release as a biomarker.

Observations:

*Capsicum* composition displayed a strong potent inhibitory effect of pancreatic lipase (PL) compared to Orlistat. 1050 for *capsicum* composition (CC1) was 5.4 (µg/ml) compared to Orlistat (0.53 µg/ml). See FIG. 1.

TABLE 2

Effect of capsicum composition on lipolysis

| Details (composition and time) | Ratio treated/non treated |
|---|---|
| Capsicum composition 1 h | 0.80 |
| Capsicum composition 2 h | 1.00 |
| Capsicum composition 4 h | 1.31 |
| Capsicum composition 24 h | 1.59 |
| Isoproterenol (positive control) | 1.60 |

*Capsicum* composition enhanced the lipolysis after 24 h treatment. The ratio of released glycerol/protein content was 1.59, compared to the positive control:isoproterenol (ratio: 1.60). See Table 2.

FIG. 1 shows the effect of *capsicum* composition on pancreatic lipase enzyme.

These observations (Table 2 and FIG. 1) suggest that *capsicum* composition has inhibitory effects on pancreatic lipase, decreases fat accumulation by adipocyte differentiation inhibition and stimulates lipolysis on adipocytes. Therefore, *capsicum* composition can be developed as a functional food in helping the treatment of postprandial lipidemia and/or prevention of weight gain and weight management.

Gene Expression Study:

3T3L1 pre-adipocytes were treated overnight with *capsicum* composition CC1. RNA was isolated and cDNA prepared. Real time PCR was performed on a selected list of genes using standard protocols.

Figure 2:
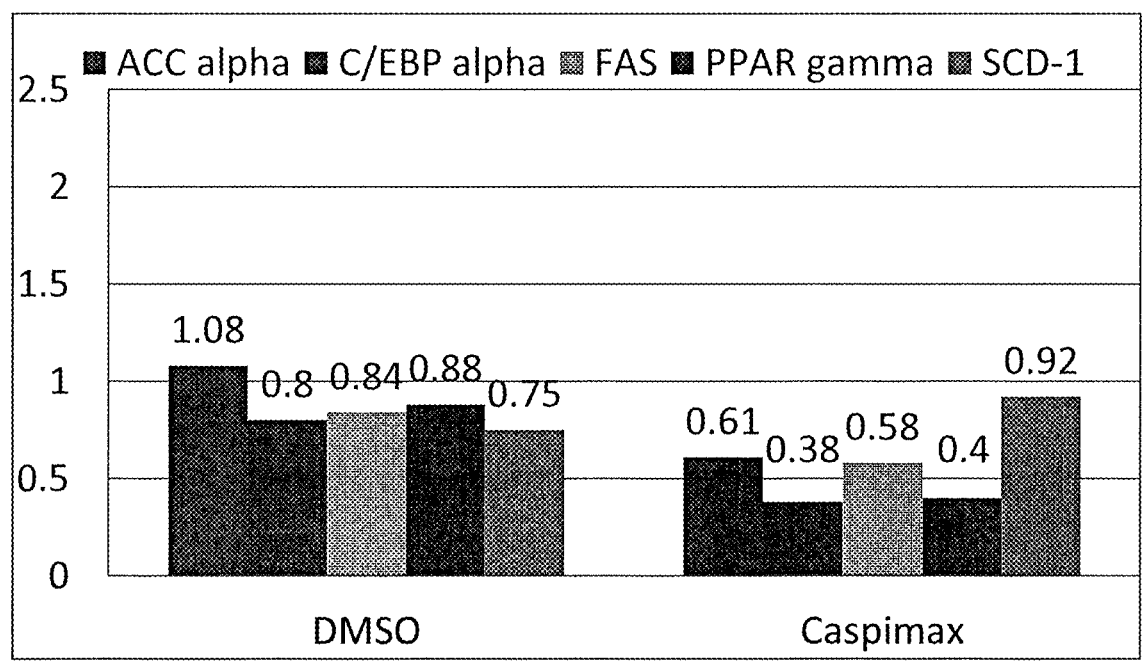
FIG. 2 shows a graph of the effect of *capsicum* composition on gene expression.

FIG. 2: Effect of *capsicum* composition on gene expression in adipocytes cells

It was observed that *capsicum* compositions exhibited reduced fat accumulation by down-regulating PPARγ and C/EBPα in 3T3L1 adipocytes . . . . Further it was seen that *capsicum* compositions also down-regulate FAS (fatty acid synthetase) and ACC alpha (Acetyl CoA carboxylase alpha) gene expression, while it up-regulates SCD-1 (Stearoyl CoA desaturase), thus indicating role in managing cardiometabolic syndrome and associated risk factors. (Capsimax represents a *capsicum* composition herein)

Example 4: Effect of *Capsicum* Composition on Cardiovascular Markers

Human Umbilical Vein Endothelial Cells (HUVEC) were purchased from Clonetics (Cambrex, Inc., Walkersville, Md., USA), defrosted and cultured in suitable growth medium. The cells were passaged three times to provide a pool of cells. Experiments were performed in six-well plates (Corning, Inc., Corning, N.Y., USA) when the cells were 80% confluent, the endothelial basal medium 2 growth media (2% fetal calf serum, with growth factors) was replaced with endothelial basal medium 2 control media (0.8% fetal calf serum, no growth factors), and then incubated for 24 h (37 C, 5% CO2). Treatments were prepared in endothelial basal medium 2 containing 0.8% fetal calf serum and antibiotics, but with no other supplements. *Capsicum* compositions were used as test samples to treat the cells. Eighteen hours after treatment RNA was extracted. Real-time PCR (polymerase chain reaction) was performed on a select list of genes using standard protocols.

Observation:

*capsicum* composition decreased VCAM1 (vascular cytoadhesion molecule-1), ICAM1 (intercellular adhesion molecule-1) and increased eNOS (Endothelial nitric oxide synthase), which is an indicative of improving cardiovascular health.

Example 5: Effect of *Capsicum* Composition on High Carbohydrate (Starch) and High Fat Diet (HFD)

A study was carried out to investigate effects of *capsicum* composition on regulating the expression of genes for metabolism in low fat/high carbohydrate (starch) diet (HSD) and high fat diet (HFD) induced obesity in rats.

High Fat diet (HFD) is referred to a diet rich in fats, especially saturated (animal or tropical oils) fats. High-fat diets typically contain about 32 to 60% of calories from fat.

High carbohydrates/starch diet (HSD) or Carbohydrate loading diet, increase carbohydrate intake to about 10 to 12 grams of carbohydrate/starch per kilogram of body weight (70 percent of daily calories).

Eight week male Wistar rats were fed on a high starch and high fat diet with and without *capsicum* composition and compared with control group for 8 weeks to induce obesity. Subsequently they were divided into different groups and were maintained on control, 10 mg/kg body weight *capsicum*, high starch diet (subdivided into group of with and without *capsicum*) and high fat diet (subdivided into group of with and without *capsicum*). Changes in the gene protein levels of gp91phox (NOX2-rabbit monoclonal antibodies), sirtuin1 (SIRT 1), nuclear factor NFkB (nuclear factor kappa-light-chain-enhancer of activated B cells), endothelial NO synthase (eNOS), p22phox Protein (human neutrophil cytochrome b light chain—CYBA) and nuclear factor erythroid 2-related factor 2 (Nrf2) were analyzed. Serum and liver TBARS (Thiobarbituric acid reactive substances) and total antioxidant capacity (TAC) were analyzed in all treatments.

Figure 3:
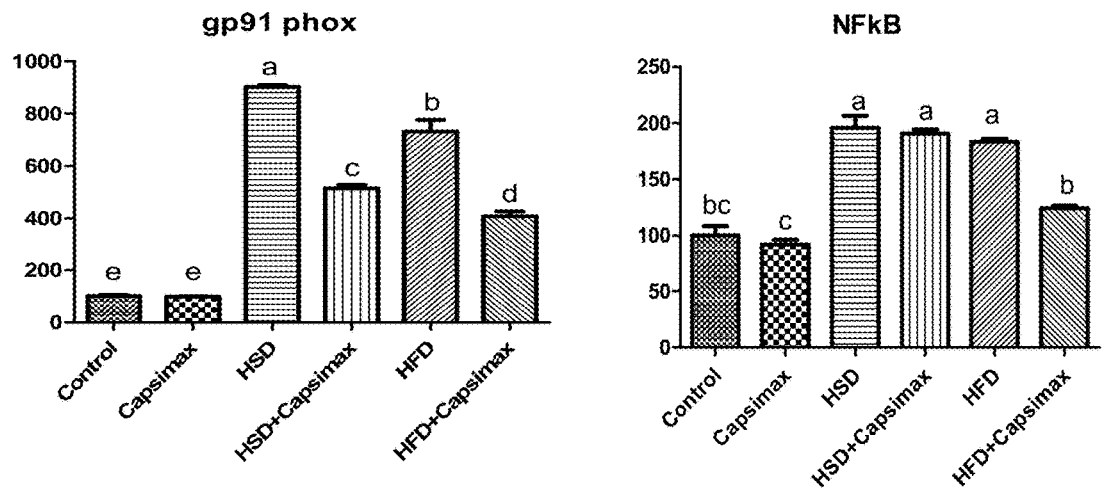
FIG. 3 shows a graph of the effect of *capsicum* compositions to decrease gp91 phox and decrease NFkB
Figure 4:
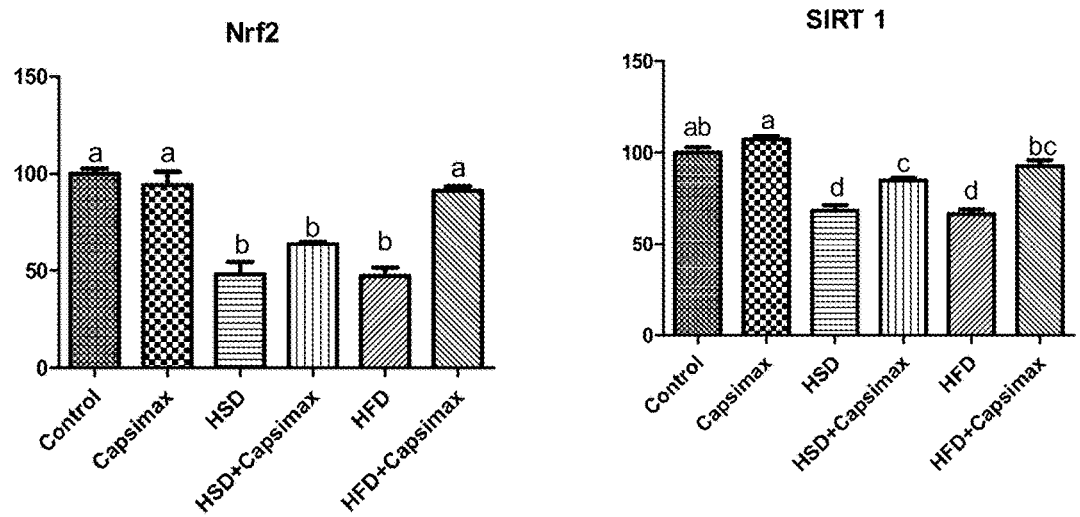
FIG. 4 shows a graph of the effect of *capsicum* compositions to increase Nrf2 and increase SIRT 1.
Figure 5:
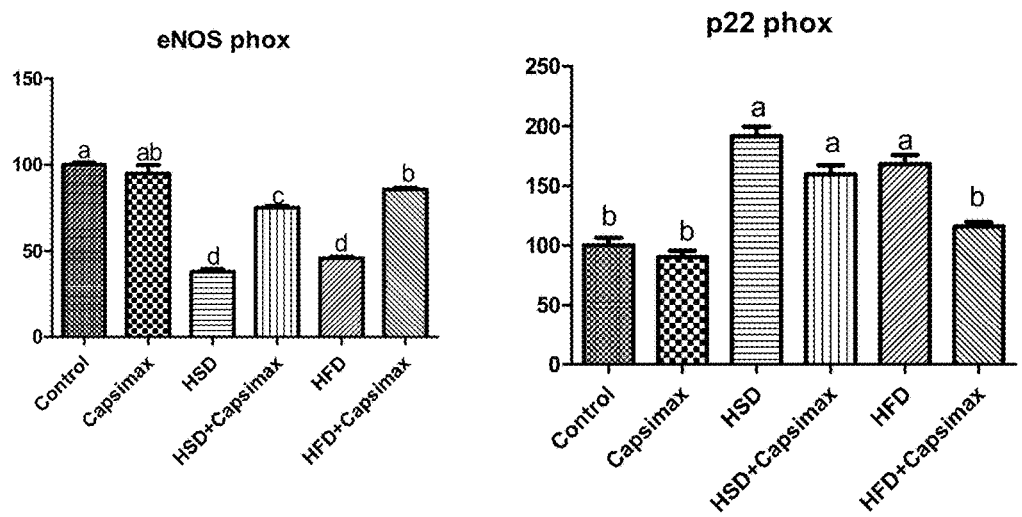
FIG. 5 shows a graph of the effect of *capsicum* compositions to increase eNOS and decrease p22 phox.

Results are shown in FIGS. 3, 4 and 5.

Observation:

Experimental diets supplemented with *capsicum* composition lowered mRNA levels of gp91phox (NOX2), NFkB, p22phox and Protein (CYBA). However, the mRNA levels of SIRT which is an important regulator of energy metabolism, Nrf2, which is an emerging regulator of cellular resistance to oxidation and, eNOS, which is a vasoprotective molecule nitric oxide (NO.) were significantly increased.

*Capsicum* composition treated groups had significant decrease in TBARS in serum and liver tissue and an increase in serum TAC. These results suggest that CAPs effectively reduce TBARS and increase TAC. These effects might be at least partially mediated via regulation of the gene proteins involved in energy metabolism, oxidative stress and vasoprotection.

Thus it was also observed that *capsicum* compositions herein can prevent low-fat/high-carbohydrate diet and high-fat diet-induced obesity by regulating the expression of genes for metabolism.

FIG. 3 shows *capsicum* compositions decrease gp91 phox and decrease NFkB.

FIG. 4 shows *capsicum* compositions increase Nrf2 and increase SIRT 1.

FIG. 5 shows *capsicum* compositions effect to increase eNOS and decrease p22 phox.

Example 6: Effect of *Capsicum* Composition on Body Indices, Glucose Management and Blood Pressure In a double blind, randomized, placebo controlled design seventy-seven (29.6±11.3 yrs, 171.2±9.8 cm, 80.9±18.9 kg, 27.4±5.4 kg/m2) apparently healthy males and females were randomly assigned by fat mass to ingest either 2 mg/kg body weight *capsicum* composition or 4 mg/kg body weight composition or placebo (maltodextrin, PLA) for 12 weeks. Subjects were requested not to make any changes to their current physical activity, provided instructions to restrict spicy foods and maintain current caloric intake. Subjects were instructed to take the pills with 8 ounces of water after breakfast. At baseline (T1), 6 weeks (T2) and 12 weeks (T3), waist and hip circumferences (waist circumference (WC), hip circumference (HC), and waist to hip ratio (WHR)), weight, appetite levels (Council on Nutrition appetite questionnaire—CNAQ) and adverse events questionnaires were administered. At baseline (T1) and 12 weeks (T3) complete blood count and complete metabolic panels were assessed. Statistical analyses utilized a two-way analysis of variance ANOVA (group×time) with repeated measures for all dependent variables ($p<0.05$).

Waist:hip ratio measurements showed a main effect for time (p=0.034) with post-hoc tests revealing a significant (p=0.024) decrease in results from baseline to 6 weeks interval. Appetite questionnaire responses indicated a significant main effect for time from T1 to T2 (p=0.004) and T1 to T3 (p=0.001) suggesting supplementation of CAP reduced appetite. Post-hoc analysis showed significant decreases in the following: PLA (T1 to T2, p=0.05), composition dose 2 mg/kg body weight (T1 to T3, p=0.018), and composition dose 4 mg/kg body weight (T1 to T2, p=0.029; T1 to T3, p=0.04). Dietary recall analysis of total caloric intake showed a significant main effect for time (p=0.019) in females at the 4 mg/kg body weight *capsicum* composition dose at T3 (12 weeks).

*Capsicum* composition dose decreased diastolic blood pressure and changes in glucose metabolism observed. No significant changes were observed in clinical blood safety markers at both doses of CAP. These findings show evidence to support that the dietary supplementation of CAP has beneficial effects on anthropometric parameters (waist and hip circumferences) and appetite suppression. The results also exhibited significant reduction in total caloric intake over 12 weeks.

Figure 6:
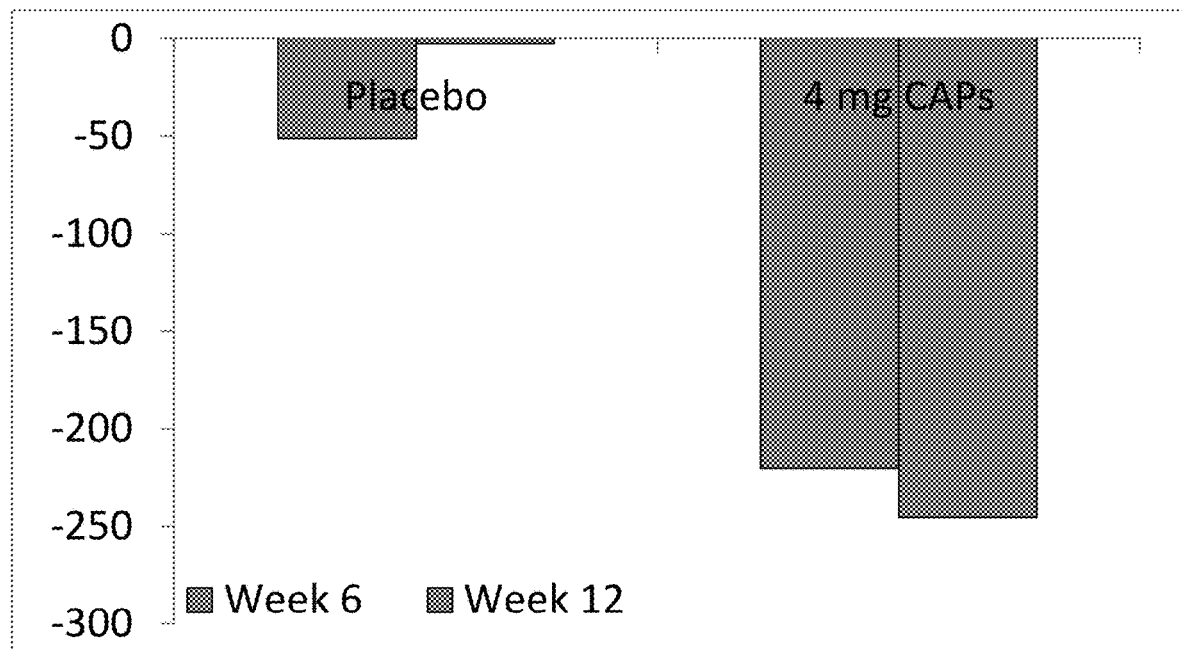
FIG. 6 shows a graph of the significant decrease in K calorie intake in females supplemented with 4 mg the composition herein.

FIG. 6 shows a graph of the significant decrease in K calorie intake in females supplemented with 4 mg CAPs.

Figure 7:
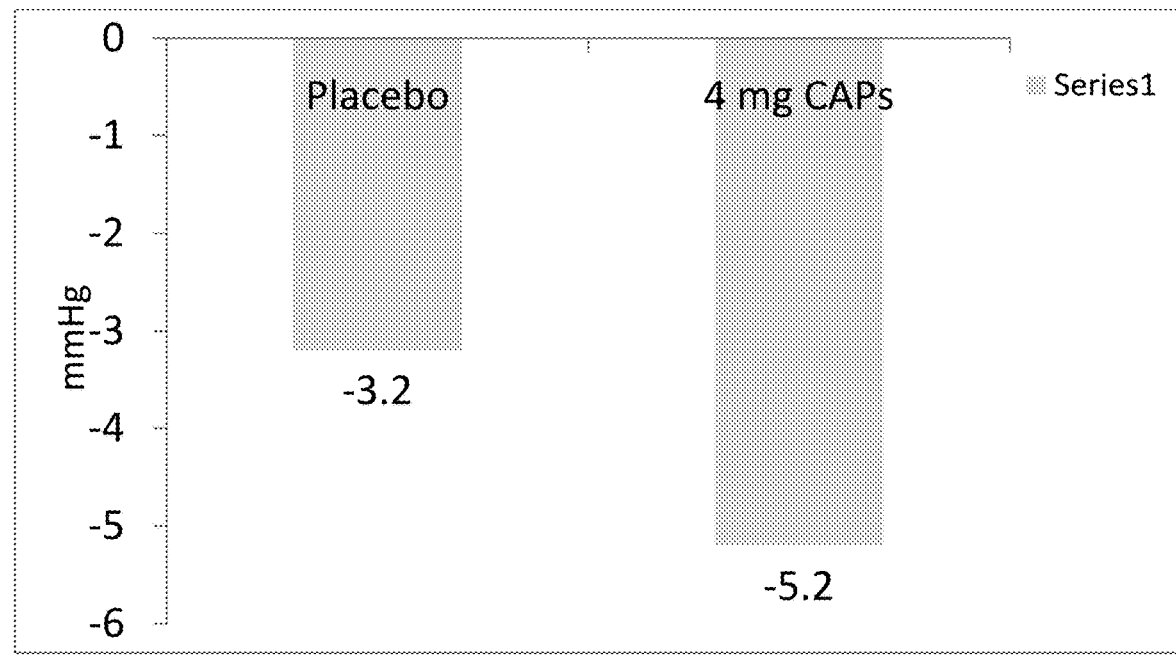
FIG. 7 shows a graph of the significant decrease in diastolic blood pressure in 4 mg the composition herein.

FIG. 7 shows a graph of the significant decrease in diastolic blood pressure in 4 mg Capsimax.

Figure 8:
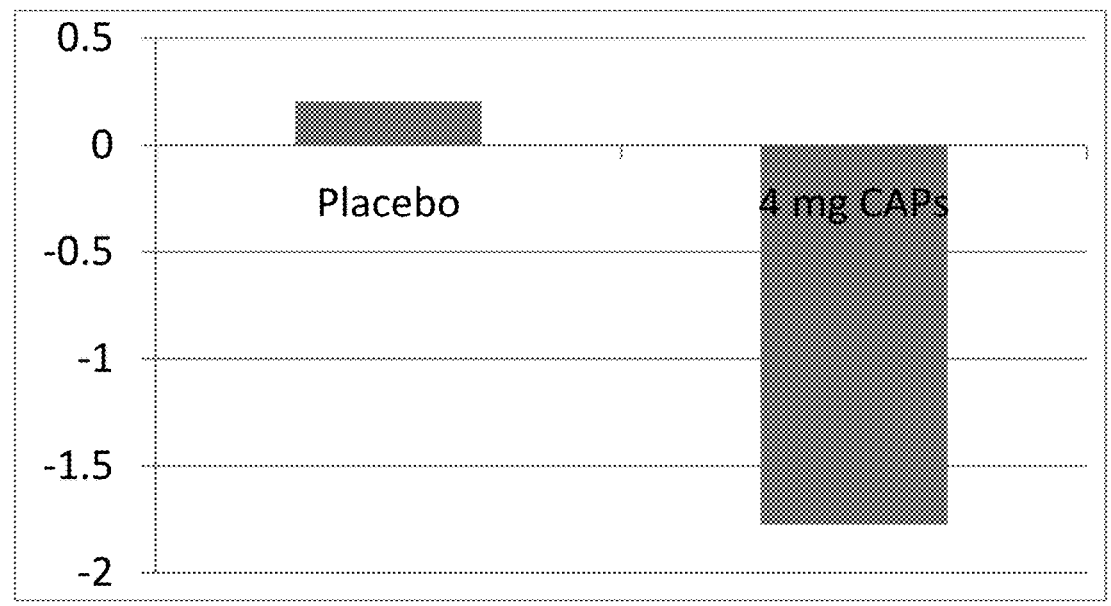
FIG. 8 shows a graph of the significant decrease in hip circumference in 4 mg of the composition herein after 12 weeks supplementation.

Even relatively small reductions in blood pressure (systolic blood pressure 10-12 mmHg, diastolic blood pressure 5-6 mmHg) substantially reduce cardiovascular risk FIG. 8 shows a graph of the significant decrease in hip circumference in 4 mg CAPs after 12 weeks supplementation.

Figure 9:
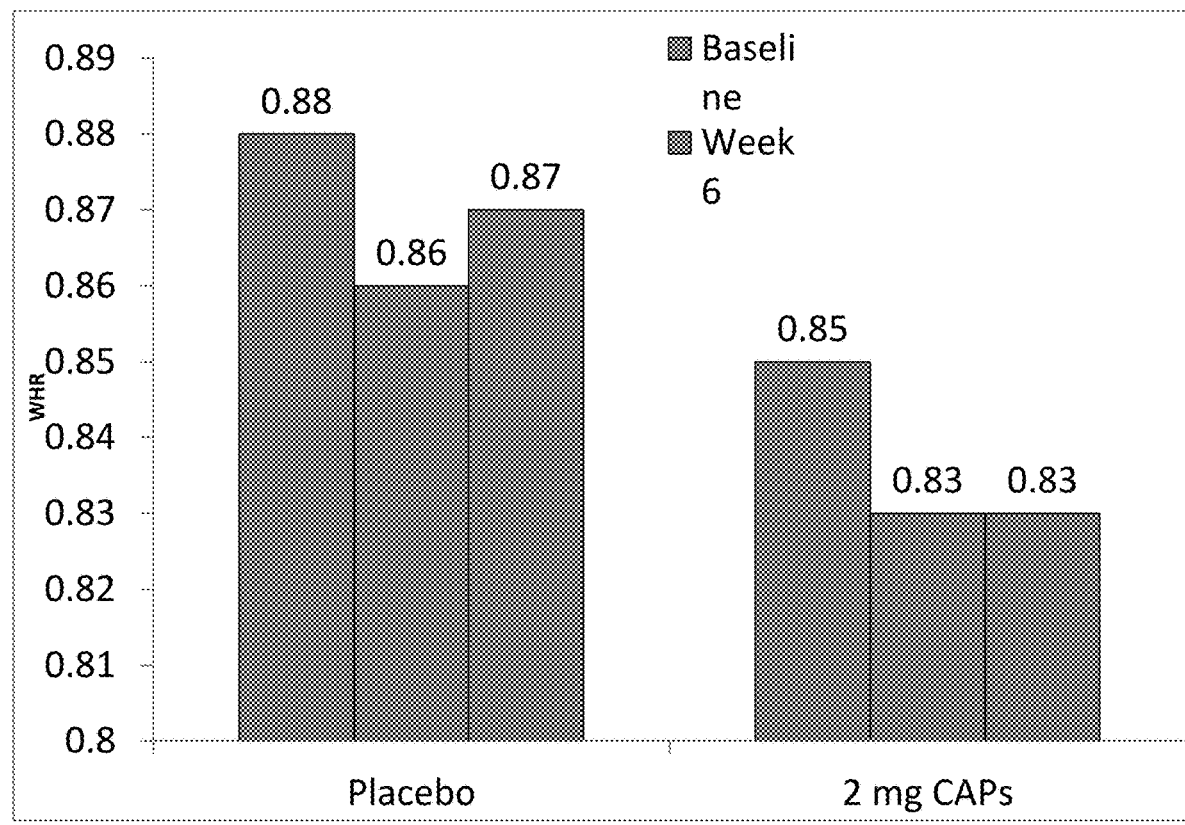
FIG. 9 shows a graph of the decrease in Waist to Hip ratio in 2 mg of the composition herein.

FIG. 9 shows a graph of the decrease in Waist to Hip ratio in 2 mg CAPs.

The invention claimed is:

1. A method of treating cardiometabolic syndrome, comprising administering, to a subject that has been fed with a diet that contains about 70% of daily calories from carbohydrates or about 32 to 60% of daily calories from fat for a period of eight weeks and has a high risk of developing or suffering from cardiometabolic disease as indicated by increased gp91 phox, p22 phox and nuclear factor kappa-light-chain-enhancer of activated B cells (NFkB), and decreased nuclear factor erythroid 2-related factor 2 (Nrf2), sirtuin1 (SIRT1), and endothelial NO synthase (eNOS), as compared to those of a subject that has not been fed with the diet, an effective amount of a *capsicum* composition which consists of non-capsaicinoids and capsaicinoids in a ratio of 1:0.1 to 1:10, and which is safe for human consumption, wherein the non-capsaicinoids consists of saponins and polyphenols and are present in a range of about 10 to 25% w/w of the total composition, and wherein the capsaicinoids comprise one or more of capsaicin, dihydrocapsaicin, homocapsaicin, nordihydrocapsaicin and N-vanillyldecanamide and the total capsaicinoids are in a range of 25 to 40% w/w of the total composition.

2. The method of claim 1, wherein the polyphenols include flavonoids and cinnamic acid derivatives, and the polyphenols are in a range of 10 to 20% w/w of the total composition.

3. The method of claim 1, wherein the administering includes regulation of risk factors including one or more of blood glucose, lipid profile, body fat, and body weight.

4. The method of claim 3, wherein the regulation is through reduction in oxidative stress and inflammatory markers.

5. The method of claim 3, wherein the regulation is through enhancement of lipolysis and inhibition of pancreatic lipase enzyme.

6. The method of claim 1, wherein the effective amount is a dose of 0.5 mg to 10 mg/kg body weight of the subject.

* * * * *